US010322067B2

(12) United States Patent
Tai et al.

(10) Patent No.: US 10,322,067 B2
(45) Date of Patent: Jun. 18, 2019

(54) DILATION DEVICE FOR PLACING CATHETER TUBES

(71) Applicant: Avent, Inc., Alpharetta, GA (US)

(72) Inventors: Kok-Ming Tai, Lawrenceville, GA (US); Donald J. McMichael, Roswell, GA (US); John A. Rotella, San Diego, CA (US); Nathan C. Griffith, Roswell, GA (US); Emily A. Reichart, Atlanta, GA (US); Courtney E. Rowe, Marietta, GA (US); Steve A. Holley, Cumming, GA (US); Edward B. Madsen, Cumming, GA (US)

(73) Assignee: Avent, Inc., Alpharetta, GA (US)

( * ) Notice: Subject to any disclaimer, the term of this patent is extended or adjusted under 35 U.S.C. 154(b) by 422 days.

(21) Appl. No.: 15/530,336

(22) Filed: Oct. 13, 2016

(65) Prior Publication Data

US 2017/0135908 A1    May 18, 2017

Related U.S. Application Data

(62) Division of application No. 13/245,577, filed on Sep. 26, 2011, now abandoned.
(Continued)

(51) Int. Cl.
| *A61M 29/00* | (2006.01) |
| *A61J 15/00* | (2006.01) |
| *A61M 25/10* | (2013.01) |
| *A61B 17/34* | (2006.01) |
| *A61M 29/02* | (2006.01) |

(Continued)

(52) U.S. Cl.
CPC .......... *A61J 15/0015* (2013.01); *A61B 17/29* (2013.01); *A61B 17/3415* (2013.01); *A61J 15/0038* (2013.01); *A61J 15/0042* (2013.01); *A61M 13/003* (2013.01); *A61M 25/09* (2013.01); *A61M 25/1002* (2013.01); *A61M 25/1011* (2013.01); *A61M 29/02* (2013.01); *A61M 2025/1013* (2013.01)

(58) Field of Classification Search
CPC ............ A61B 17/3415; A61B 17/3423; A61J 15/003; A61J 15/0015; A61M 2029/025; A61M 2025/1059; A61M 2025/1068; A61M 2025/1072
See application file for complete search history.

(56) References Cited

U.S. PATENT DOCUMENTS

| 5,458,583 A | 10/1995 | McNeely et al. |
| 6,019,746 A | 2/2000 | Picha et al. |

(Continued)

FOREIGN PATENT DOCUMENTS

| WO | WO 2002/019890 A2 | 3/2002 |
| WO | WO 2008/154533 A1 | 12/2008 |
| WO | WO 2011/159590 A2 | 12/2011 |

*Primary Examiner* — Elizabeth Houston
*Assistant Examiner* — Kankindi Rwego
(74) *Attorney, Agent, or Firm* — Dority & Manning, P.A.

(57) ABSTRACT

A stoma dilation device that includes a tubular support defining a continuous pathway through the device; an inflatable dilation balloon located on the tubular support, the inflatable dilation balloon including a dilation region forming a first portion of the device and a retention region forming a second portion of the device; and a balloon inflation lumen. The retention region of the balloon is configured to have a diameter upon full, unrestrained inflation that is greater than the diameter of the dilation region.

19 Claims, 3 Drawing Sheets

Related U.S. Application Data

(60) Provisional application No. 61/386,793, filed on Sep. 27, 2010, provisional application No. 61/446,229, filed on Feb. 24, 2011.

(51) Int. Cl.
*A61B 17/29* (2006.01)
*A61M 13/00* (2006.01)
*A61M 25/09* (2006.01)

(56) References Cited

U.S. PATENT DOCUMENTS

| | | |
|---|---|---|
| 6,236,879 B1 | 5/2001 | Konings |
| 6,293,924 B1 | 9/2001 | Bagaoisan et al. |
| 7,137,993 B2 | 11/2006 | Acosta et al. |
| 7,273,056 B2 | 9/2007 | Wilson et al. |
| 7,396,354 B2 | 7/2008 | Rychnovsky et al. |
| 7,757,695 B2 | 7/2010 | Wilson et al. |
| 8,795,311 B2 | 8/2014 | Griffith et al. |
| 9,339,442 B2 | 5/2016 | Tai et al. |
| 2003/0100909 A1 | 5/2003 | Suzuki |
| 2003/0225312 A1 | 12/2003 | Suzuki et al. |
| 2006/0095066 A1 | 5/2006 | Chang et al. |
| 2007/0225677 A1 | 9/2007 | Rowe et al. |
| 2007/0255209 A1 | 11/2007 | Crooms et al. |
| 2008/0167606 A1 | 7/2008 | Dann et al. |
| 2008/0194973 A1 | 8/2008 | Imam |
| 2008/0228066 A1 | 9/2008 | Waitzman |
| 2008/0287983 A1 | 11/2008 | Smith et al. |
| 2009/0281379 A1 | 11/2009 | Binmoeller et al. |
| 2009/0318757 A1 | 12/2009 | Singh |
| 2009/0318798 A1 | 12/2009 | Singh et al. |
| 2010/0087706 A1 | 4/2010 | Syed et al. |
| 2010/0198005 A1 | 8/2010 | Fox |

DILATION DEVICE FOR PLACING CATHETER TUBES

CROSS-REFERENCE TO RELATED APPLICATIONS

This application is a divisional of and claims priority to U.S. application Ser. No. 13/245,577, filed Sep. 26, 2011, which claims the benefit of priority from U.S. Provisional Application No. 61/386,793 filed on Sep. 27, 2010 and U.S. Provisional Application No. 61/446,229 filed on Feb. 24, 2011, the contents of which are incorporated herein by reference.

BACKGROUND

This disclosure relates to catheters such as feeding tubes and their placement in the body of a patient.

Numerous situations exist in which a body cavity needs to be catheterized to achieve a desired medical goal. One relatively common situation is to provide nutritional solutions or medicines directly into the stomach or intestines. A stoma is formed in the stomach or intestinal wall and a catheter is placed through the stoma. This surgical opening and/or the procedure to create the opening is commonly referred to as "gastrostomy". Feeding solutions can be injected through the catheter to provide nutrients directly to the stomach or intestines (known as enteral feeding). A variety of different catheters intended for enteral feeding have been developed over the years, including some having a "low profile" relative to the portion of the catheter which sits on a patient's skin, as well as those having the more traditional or non-low profile configuration. These percutaneous transconduit catheters (sometimes referred to as "percutaneous transconduit tubes") are frequently referred to as "gastrostomy catheters", "percutaneous gastrostomy catheters", "PEG catheters" or "enteral feeding catheters". U.S. Pat. No. 6,019,746 for a "Low Profile Balloon Feeding Device" issued to Picha et al. on Feb. 1, 2000, provides an example of one device.

These catheters are frequently placed in a procedure called percutaneous endoscopic gastrostomy (frequently referred to as PEG). Traditionally, a PEG tube is placed using endoscopic guidance or x-ray guidance. In a conventional PEG procedure that places a PEG tube into a patient's stomach, an endoscope is used to observe that the patient's esophagus is unobstructed and to inspect and inflate the stomach to see that the area selected for the gastrostomy can be distended.

If the location is suitable, this spot is selected. Prior to placement of any feeding tube, it has been found that it is useful to anchor the anterior wall of the gastric lumen (e.g., the stomach) to the abdominal wall as a step prior to creating the stoma tract through the two. Insufflation of the gastric lumen has also been found to be successful in maintaining the lumen in close proximity of the abdominal wall in some procedures. This procedure is also applicable to jejunostomy or gastro-jejunostomy as well as the gastrostomy procedure referred to above. Similar procedures may also be applicable or desirable for other catheter tubes such as peritoneal drainage tubes.

After the wall of the lumen is anchored, a needle is inserted into the patient in the area in the appropriate location. Additionally, a small incision may be made in the skin. An endoscopist will then typically watch through the endoscope as a needle pushes through the patient's skin, then through the abdominal wall, and enters the gastric lumen in the selected area to form a needle tract. A guide wire is passed through the needle into the gastric lumen (e.g., the stomach). The endoscopist will use an endoscopic snare to grasp the guide wire firmly. The snare, passed through the working channel of the endoscope, firmly grabs the guide wire. Both the endoscope and snare are then withdrawn together through the patient's mouth, pulling the guide wire with them. The end of the guide wire that extends out from the patient's mouth is subsequently attached to a PEG tube and the other end of the guide wire remains outside the patient's skin in the abdominal region.

The PEG tube is guided into the patient's mouth (while the endoscope is completely removed from the patient) and pulled into the patient's gastric lumen as the guide wire is pulled from the end that remains outside the patient's skin. Once the PEG tube is in the gastric lumen, it is pulled partially through the gastric and abdominal walls until a bumper of the PEG tube is snug against the gastric mucosa. However, in order for the PEG tube to be pulled partially through the gastric and abdominal walls and skin, the original needle tract must be dilated. This dilation is carried out with conventional dilation devices that employ a tapered dilator at the distal end of the PEG tube so that it dilates the opening as it is pulled through the gastric mucosa. During such dilation, the endoscope is again passed into the patient and subsequently used to visually observe that the bumper of the PEG tube is snug against the gastric mucosa.

In other conventional PEG tube placement procedures, endoscopy is not used at all. Instead, x-ray techniques are used to help select a particularly suitable location in the patient's body (e.g., the stomach) for the introduction of the PEG tube. X-ray is used for guiding the PEG tube placement and for inspecting the PEG tube's final position.

In yet another procedure, known as gastropexy, a needle is used to pierce a patient's abdominal wall to place one or more fasteners in a patient's gastric lumen. A fastener, such as a "T-bar" fastener, carried at or near the tip of the needle is desirably deployed by the needle so that it can be positioned against an inner wall of the gastric lumen. A tensioning suture is connected to the fastener and, at an opposite end of the suture on the outer surface of the patient's body, the suture is desirably also connected to a suture holder, which permits adjustment of the tension on the suture. In this manner, when the suture is tensioned a patient's gastric lumen wall is more closely positioned to the outer surface of the patient's body, and the gastric lumen is stabilized in a position. Usually, at least three and desirably four fasteners are placed in a triangular, square, or diamond-shaped configuration through a patient's skin and into the gastric lumen.

While there are some problems associated with these conventional procedures including an increased risk of esophageal trauma associated with multiple passes of an endoscope into and out of a patient or placement of the PEG in an improper location, one significant problem is related to the additional complications of anchoring the wall of the gastric lumen to the abdomen. It would be desirable to avoid the complications of the additional steps of such a procedure and/or the additional trauma caused by mechanically anchoring (even temporarily) the wall of the gastric lumen to the abdomen. While avoiding these complications may be desirable, suitable devices or procedures are lacking.

Accordingly, there is a need for a device, system and method for placing a non-vascular catheter tube such as a PEG tube in a patient that reduces these risks and trauma and is easy to perform.

SUMMARY

In response to the difficulties and problems discussed herein, this disclosure describes a dilation device and dilation system. The dilation device is an inflatable device that is used for placing catheter tubes in a non-vascular lumen, desirably under direct visualization using an endoscope.

According to this disclosure, a conventional endoscope is advanced into the stomach to insufflate and allow palpation to locate an appropriate site. Once the appropriate site is located, a needle is inserted into the stomach through the abdomen from outside the body to form a needle tract. A guide wire is then introduced into the stomach through the needle, and a system is provided for: positioning a dilation device in the needle tract; maintaining the dilation device in the desired position; dilation of the needle tract, and removal of the dilation device.

The dilation device includes an inflatable balloon including a dilation region forming a first portion of the device and a retention region forming a second portion of the device, an inflation lumen to inflate and deflate the inflatable balloon, a tubular support, and a continuous pathway through the device that accommodates a guide wire. The inflatable balloon may be compliant, semi-compliant, or non-compliant.

The inflatable balloon (also referred to as a "dilation balloon") is located towards the distal end of the device. The dilation balloon includes a distal section and an opposing proximal section. The dilation balloon has a length with a pre-determined diameter upon full inflation to fit a specific sized catheter tube device. Alternatively, the dilation balloon may be dilated to various effective diameters using respectively different inflation pressures to fit various catheter tubes. The proximal section of the dilation balloon (that portion of the dilation balloon that is positioned in the non-vascular lumen) may be designed to have substantially the same diameter features of the distal section or it may have a section with a larger diameter than any diameters of the distal section. The balloon section with the largest diameter is referred to as the "retention section" or the proximal retention balloon component". Once this section is inflated, it functions to provide retention of the dilation device within the non-vascular lumen (e.g., the stomach). The proximal retention balloon component may be compliant, semi-compliant, or non-compliant. The inflatable balloon (i.e., the dilation balloon) has two opposing open ends. These open ends are attached to the tubular support.

The tubular support of the dilation device supports the dilation balloon. The dilation device also has at least one inflation lumen to inflate and deflate the dilation balloon component. It is contemplated that any of the inflation lumens included in the dilation device can serve as the tubular support for the dilation balloon. In other words, the tubular support may define the relevant inflation lumens.

The dilation device may have a continuous single pathway through its entirety to accommodate a guide wire. This pathway may include the inflation lumen for the dilation balloon and the tubular support; or it may be a separate lumen that is contained within the walls of an inflation lumen, the tubular support; or combinations thereof.

According to this disclosure, the dilation device may be utilized in "inside-out" or "outside-in" dilation procedures. Inside-out dilation procedures involve attachment of the dilation device to the guide wire outside of the patient's mouth or inside the non-vascular lumen (e.g., the stomach or other space). A non-limiting example of attachment outside the patient's mouth may involve the following steps: insertion of an endoscope that extends from outside the mouth to inside the stomach; conventional placement of a guide wire through the skin, abdominal wall and stomach wall utilizing a needle; insertion of a standard endoscopic forceps or an endoscopic snare through the working channel of the endoscope; using the forceps or snare to grasp the guide wire portion that is in the stomach and then pulling the guide wire through the working channel of the endoscope and out of the patient's mouth (unlike current practice where the entire endoscope is removed from the patient); securely attaching the end of the dilation device that is closest to the dilation balloon (not the retention balloon portion of the dilation device) to the end of the guide wire that extends from the patient's mouth; pulling the guide wire and attached dilation device back through the working channel of the endoscope so that the dilation balloon exits the working channel into the stomach via the guide wire portion that remains outside the skin. An non-limiting example of attachment of the dilation device to the guide wire inside the patient's stomach may involve the following features and/or steps: the dilation device contains a fixture (magnet, hook, loop, snare, etc.) at the end that is closest to the dilation balloon (the side that enters the mouth first); the dilation device is pushed through the working channel of the endoscope so that the fixture exits the working channel; the fixture is attached under visualization of the endoscope by connecting the fixture to the guide wire (that was inserted through the needle); pulling the guide wire portion that remains outside the skin so that the dilation device pulls through the working channel and into the stomach. Regardless of the steps used to place the dilation device in the stomach, after placement in the stomach it is pulled into and partially through the needle tract so that at least a portion of the deflated dilation balloon extends through the abdominal tissue and the skin and the retention balloon resides in the stomach.

Outside-in dilation procedures differ from inside-out procedures in that they do not pass the dilation device through the working channel of the endoscope in order to position the dilation device in the stomach, nor is there any need to attach the dilation device to a guide wire that extends from the patient's stomach through the mouth. Outside-in procedures may involve the following steps: insertion of an endoscope that extends through the mouth to inside of the stomach; conventional initial placement of a guide wire through the skin, abdominal wall, and stomach wall through an inserted needle and then removal of the needle with the guide wire in place; mounting the dilation device over the end of the guide wire that is outside of the patient's skin; partial insertion of the dilation device into the needle tract so that the retention balloon enters the stomach before any portion of the dilation balloon.

In positioning the dilation device, the dilation balloon must be in a deflated state so that the dilation device easily slides through the working channel of the endoscope and/or it penetrates the needle tract without excessive force. The dilation device in this deflated state desirably wraps and folds around the tubular support as much as possible to minimize the effective cross-sectional area of the dilation device during insertion through the endoscope and/or needle tract. Such folding and wrapping is achieved by intentionally folding the balloon walls in pre-planned arrangements, via the use of a pleater and/or folder manufacturing apparatus, or by random overlapping and folding afforded by the flexible nature and thinness of the balloon walls.

According to an aspect of this disclosure, the dilation device contains only one balloon. The dilation balloon of the dilation device is inflated by gradually introducing controlled amounts of fluid (e.g., liquid or gas) to increase pressure in this balloon. As previously described, the dilation balloon may have a length of a single diameter or it may have varying diameters. The portion of the balloon that has a length of a single diameter is placed in the needle tract and inflates radially to provide atraumatic dilation (as compared to serial dilation) of the entire needle tract to create the stoma tract. The proximal retention balloon component portion of the device inflates inside the stomach and not in the needle tract. It is used to stabilize the device and to help prevent the device from pulling out of the stoma tract during the procedure.

A better understanding of the above and many other features and advantages of the liquid dispensing device with flow indicator may be obtained from a consideration of the detailed description of this disclosure below, particularly if such consideration is made in conjunction with the appended drawings.

BRIEF DESCRIPTION OF THE DRAWINGS

In FIG. 3A the inflatable dilation balloon is in position with the retention portion within the lumen but the lumen is not snugly against the inside of the abdominal wall. In FIG. 3B the gastric lumen has been pulled snugly against the inside of the abdominal wall.

In FIG. 4A, the catheter tube is shown fitting over the fully or partially inflated dilation region through the dilated stoma tract and into the portion of the lumen stabilized by the inflated retention region. FIG. 4B illustrates the stoma dilation device deflated and at least a portion of the device being withdrawn through the catheter tube.

DETAILED DESCRIPTION

Reference will now be made to the drawings in which the various elements of the present disclosure will be given numeral designations and in which the disclosure will be discussed so as to enable one skilled in the art to make and use the disclosure. It is to be understood that the following description is only exemplary of the principles of the present disclosure, and should not be viewed as narrowing the pending claims. Those skilled in the art will appreciate that aspects of the various embodiments discussed may be interchanged and modified without departing from the scope and spirit of the disclosure.

Since the stomach is a common example of a non-vascular lumen, for the purpose of describing this disclosure, the use of the term "gastric lumen" or "stomach" is representative of all other non-vascular lumens or spaces (e.g., duodenum, jejunum, ileum, peritoneal cavity, etc.), unless otherwise specified.

Figure 1:
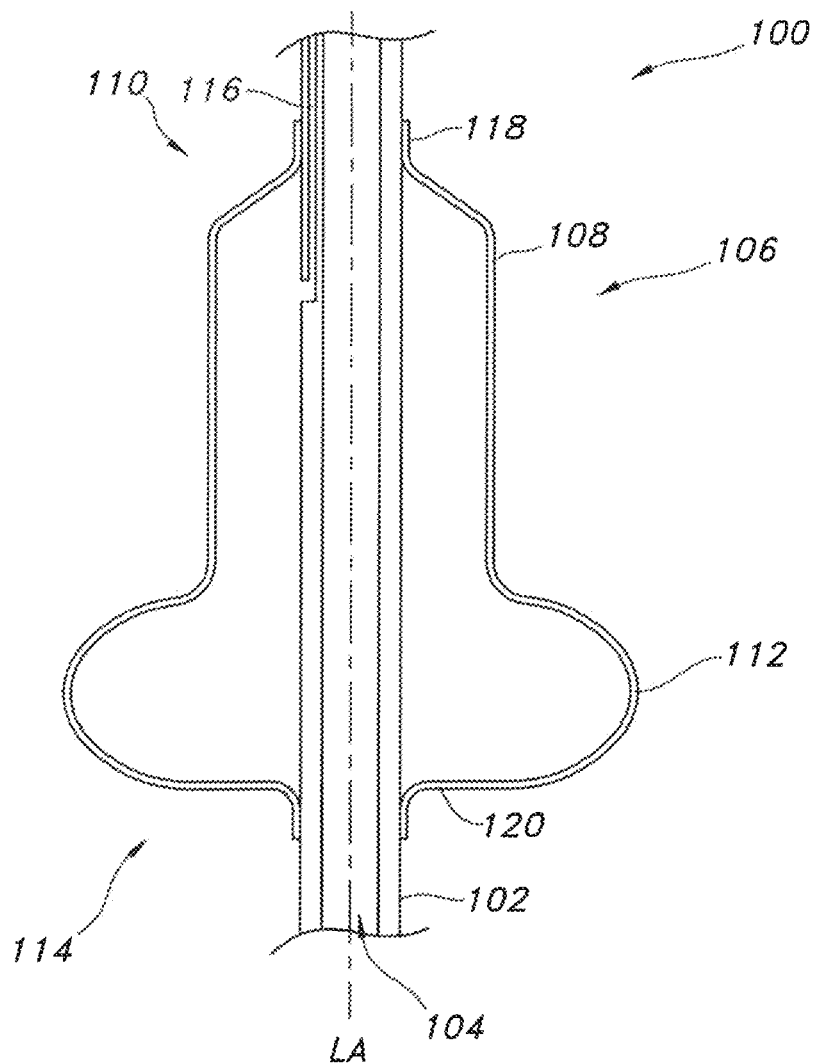
FIG. 1 is a side cross-sectional view illustrating an exemplary dilation device that has a tubular support upon which is mounted the inflatable dilation balloon.

Turning now to the drawings, there is shown at FIG. 1 in side, cross-sectional view, an exemplary stoma dilation device 100 that includes a tubular support 102 defining at least one continuous pathway 104 through the device. The continuous pathway is configured to accommodate a guide wire.

The tubular support 102 has a length, width and a longitudinal axis "LA". The tubular support 102 should be flexible but not too flexible as to readily collapse or kink when pressure is applied radially or axially. The width of the tubular support should be sufficiently small that it may fit in the working channel of an endoscope. For example, the tubular support may have a width of from about 0.2 to about 2 millimeters. More desirably, the tubular support may have a width of from about 0.5 to about 1.75 millimeters. The tubular support may be made of a variety of suitable materials. Exemplary materials include thermoplastic polyurethanes such as TECOFLEX® medical-grade aliphatic polyether polyurethanes available from Lubrizol Advanced Materials, Inc., Thermedics™ Polymer Products, Wilmington, Mass.

The device 100 includes an inflatable dilation balloon 106 located on the tubular support 102 having at least one inflatable dilation section 108 at a distal portion 110 of the device and at least one inflatable retention balloon component 112 located on a proximal portion of the device 114 (i.e., the proximal retention balloon component 112). The dilation balloon 106 has at least one dilation balloon inflation lumen 116 to inflate and deflate the dilation balloon. Desirably, the inflation lumen 116 is integrated in the tubular support 102. In this regard, the tubular support 102 may define multiple lumens. That is, the tubular support may define a continuous pathway 104, at least one dilation balloon inflation lumen 116 to inflate and deflate the dilation balloon 106. It is contemplated that the inflation lumens may be separated from the tubular support and be in the form of pilot tubes or the like.

According to this disclosure, the proximal retention balloon component 112 is configured to have an effective cross-section upon full, unrestrained inflation that is greater than the largest cross-sectional diameter of the dilation section 108 upon inflation as is generally illustrated in FIG. 1. The dilation section 108 of the balloon has a length and a circular cross-section with a pre-determined diameter upon full inflation to fit a specific sized catheter tube device. Alternatively, the dilation section 108 may be dilated to various effective diameters using respectively different inflation pressures to fit various catheter tubes. As a non-limiting example, the effective inflated diameter of the dilation section 108 may range from about 3 to about 10 millimeters. As another non-limiting example, the effective inflated diameter of the dilation section 108 may range from about 2 to about 8 millimeters. An inflated dilation balloon with a length and with a non-circular cross section along the length, e.g. elliptical or oval, is also contemplated.

The proximal portion 114 of the dilation balloon 106 (that portion of the dilation balloon that is positioned in the non-vascular lumen) incorporates the retention section 112 (also referred to as the "proximal retention balloon component") having a substantially larger cross section or diameter than any diameters of the dilation section 108. Generally speaking, the proximal retention balloon component may have a cross section or diameter that is about 1.5 times to about 3 times the diameter of the dilation section 108. Once this proximal retention balloon component 112 is inflated, it functions to stabilize the wall of the lumen and/or provide retention of the dilation device within the non-vascular lumen (e.g., the stomach).

The proximal retention balloon component 112 may have a circular or non-circular cross section as long as it is able to function as described above. The retention balloon may have or lack a cross section with one axis of symmetry. The proximal retention balloon component 112 may, for example, have a square, rectangular, triangular, elliptical, oval or other geometric. Alternatively and/or additionally the proximal retention balloon component 112 may incorporate lobes, fingers or projections that contribute to its cross-section so it is greater than the diameter of the dilation section 108. The dilation balloon 106 desirably includes two opposing open ends. The open ends may be attached to the tubular support. The dilation balloon 106 may have open ends 118 and 120.

The dilation balloon may be formed of materials such that the balloons are compliant, semi-compliant, or non-compliant. That is, the balloon may be relatively elastic (e.g., compliant) so that it stretches as well as expands upon inflation. The balloon may also be somewhat elastic (e.g., semi-compliant) so that it expands but has limited stretch upon inflation. The balloon may be inelastic (e.g., non-compliant) so that it expands without significant stretch upon inflation. Desirably, the balloons may be formed of polyurethane material identified as Pellethane® 2363-90A, available from Lubrizol Advanced Materials, Inc., Thermedics™ Polymer Products.

Figure 4A:
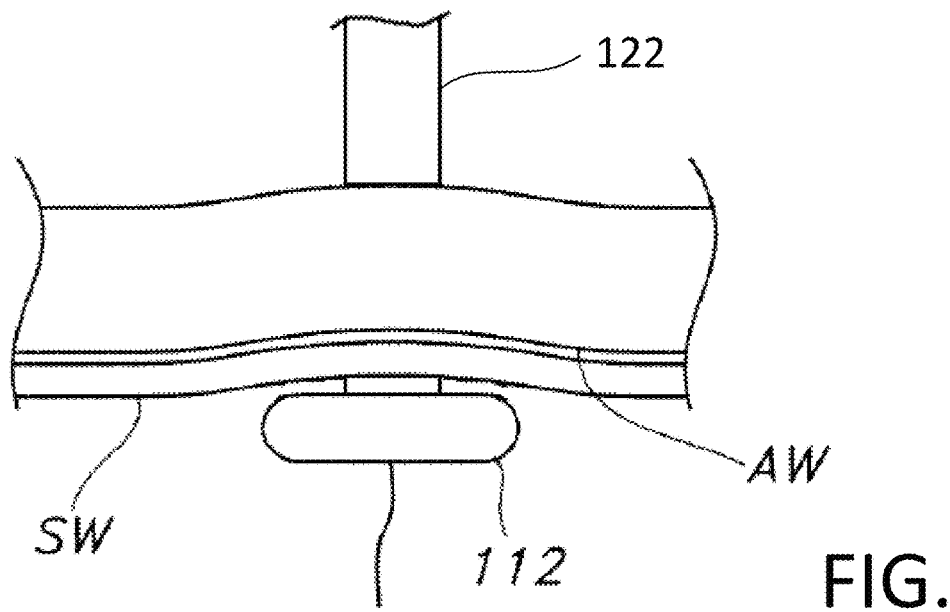
FIGS. 4A and 4B are side cross-sectional views of an exemplary catheter tube inserted through a dilated stoma tract in the lumen wall and abdominal wall.
Figure 4B:
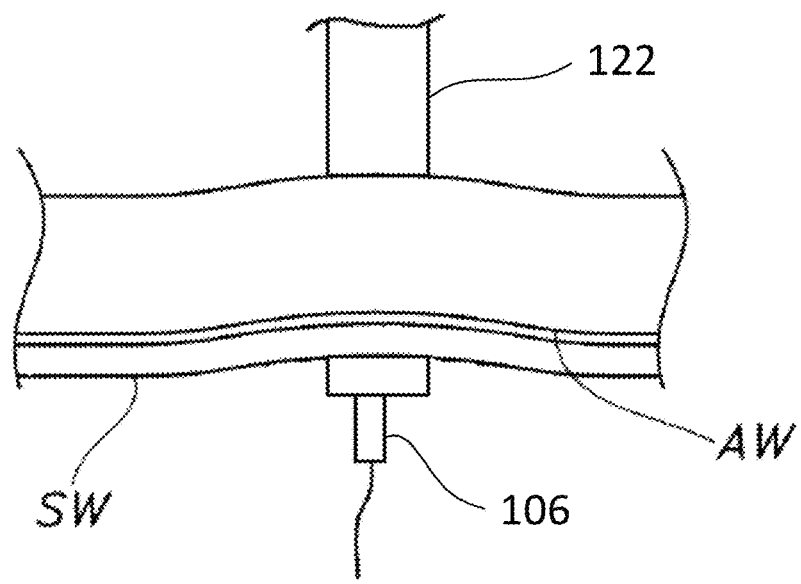

This disclosure also covers a system for dilating a stoma and inserting a non-vascular catheter tube, the system includes a stoma dilation device as described above. Referring to FIGS. 4A and 4B, the system also includes a non-vascular catheter tube 122 configured to fit over the fully or partially inflated dilation balloon 106 (i.e., the dilation section 108) through the dilated stoma tract and into the portion of the non-vascular lumen stabilized by the retention section (i.e., the proximal retention balloon component). According to the system, the stoma dilation device is configured to be deflated and at least a portion of the device withdrawn through the non-vascular catheter tube.

In an exemplary and non-limiting description of a placement of the device, an endoscope may be advanced into a non-vascular lumen (e.g., the stomach) to insufflate and allow palpation to locate a catheter tube location site (e.g., a PEG location site). Once the site is located, a needle may be inserted into the stomach through the abdomen and a guide wire may be introduced into the stomach through the needle.

Standard endoscopic forceps, an endoscopic snare, or a balloon attachment fixture may be inserted through the working channel of the endoscope. The forceps, snare or fixture is used to grasp the guide wire and the guide wire is pulled up through the working channel of the endoscope and out of the patient's mouth.

A dilation device with its attached inflation lumen is secured to the end of the guide wire and is pulled through the working channel of the endoscope using the guide wire and into the stomach. The dilation device may have a dilation balloon having a distally located dilation section having pre-determined volume and diameter upon full inflation and a proximal retention balloon component having a diameter upon full inflation that is greater than the diameter of the dilation section. When these balloons are in a folded or tightly wrapped state, the dilation device has a diameter that fits within the working channel of the endoscope. Typically, the diameter is in the range of about 2 millimeters or less.

Figure 2:
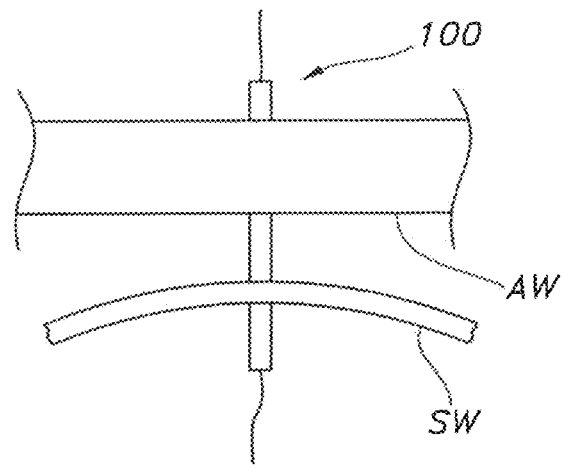
FIG. 2 is a side cross-sectional view illustrating the position of an exemplary dilation device pulled through the gastric lumen wall and abdominal wall prior to inflation of the device.

The needle is removed from the stomach, while retaining the guide wire in the needle tract. The dilation device is pulled up into and partially through the needle tract so that it reaches the abdominal tissue and the skin on the exterior of the patient as illustrated in FIG. 2.

Figure 3A:
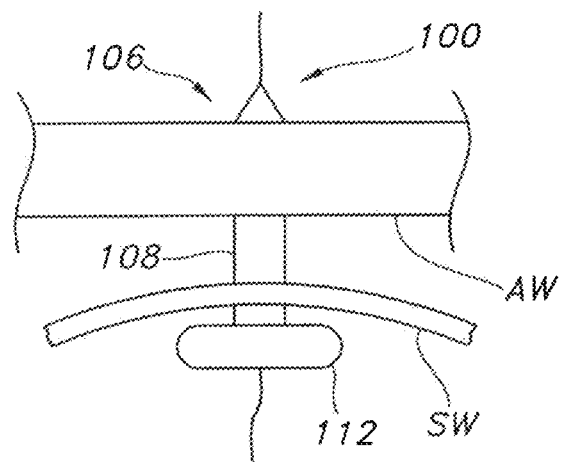
FIGS. 3A and 3B are side cross-sectional views of an exemplary dilation device showing an inflated dilation balloon and inflated retention stabilizing the lumen wall against the abdominal wall.
Figure 3B:
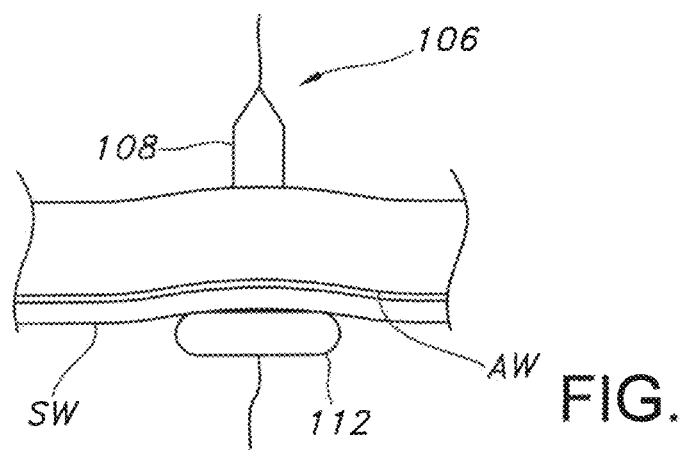

Referring now to FIGS. 3A and 3B, the dilation balloon 106 of the dilation device 100 is then inflated by gradually introducing controlled amounts of fluid (e.g., liquid or gas) to increase pressure in the balloon so the dilation section 108 smoothly and gradually expands the needle tract into a stoma tract. The proximal retention balloon component 112 of the dilation balloon 106 is also inflated as the dilation section 108 is inflated. When the proximal retention balloon component 112 becomes larger than the dilation section 108 and expands to full inflation, it stabilizes the stomach wall "SW" by bringing it up against the wall of the abdomen "AW" as illustrated in FIG. 3B. According to an aspect of this disclosure, the fully inflated diameters of the dilation balloon may be selected from a range to match the diameter of the catheter tube device 122 (e.g., the PEG device) that will be inserted. As shown in FIG. 1 and FIGS. 3A and 3B, the dilation balloon 106 can have variable diameters such that the dilation section 108 may have at least one diameter (s) and the retention section 112 (the proximal retention balloon component) may have at least one diameter that is greater than the dilation section 108.

After the dilation device has its affixed balloon fully inflated, a peel-away sheath is placed over the distal-most portion of the dilation device (i.e., from the outside of the patient). The dilation balloon of the dilation device is deflated by only a small amount (e.g. partially deflated) to allow the peel-away sheath to pass over the distal end of the dilation device and through the stoma tract into the stomach.

A catheter tube 122 (e.g., a PEG device) is then threaded over the guide wire and the distal end of PEG device is inserted through the peel away sheath. The distal end of the PEG device 122 is now in a position to hold the gastric lumen against the abdominal wall so the dilation balloon 106 may be fully deflated and withdrawn through the peel-away sheath. Note that the syringe inflation connector must be cut off of the inflation lumen in order to withdraw the dilation device through the abdominal wall. The peel-away sheath is then separated and removed from the stoma tract. Any other placement tools are removed, and the retainer (not shown) on the distal, in-dwelling end of the PEG device 122 holds the PEG device in place.

Alternatively, as shown in FIGS. 4A and 4B, the PEG device 122 may be inserted over the deflated dilation balloon 106 without the use of the peel away sheath. This places the PED device in a position to hold the gastric lumen against the abdominal wall so the dilation balloon may be fully deflated and withdrawn through the PEG device.

In yet another alternative, the dilation device, once it has its balloon completely deflated and while it is still attached to the guide wire, may be removed through the working channel of the endoscope by withdrawing the guide wire through the working channel of the endoscope. This requires the PEG to be installed in the manner described above, e.g., partial deflation of the dilation balloon and installation of the PEG through the peel-away sheath prior to dilation device removal.

While this disclosure has been described in connection with certain preferred embodiments it is to be understood that the subject matter encompassed by way of this disclosure is not to be limited to those specific embodiments. On the contrary, it is intended for the subject matter of this disclosure to include all alternatives, modifications and equivalents as can be included within the spirit and scope of the following claims.

We claim:

1. A method of placing a PEG device, the method comprising:
   advancing an endoscope through a patient's mouth into a non-vascular lumen of a patient to insufflate and allow palpation to locate a PEG tube location site;
   inserting a needle at the PEG tube location site through the non-vascular lumen, wherein inserting the needle forms a needle tract and introducing a guide wire through the needle;
   inserting standard endoscopic forceps, an endoscopic snare, or a balloon attachment fixture through the working channel of the endoscope;
   grasping the guide wire and pulling the guide wire up through the endoscope and out of the patient's mouth;
   securing a dilation device with its attached inflation lumen to the end of the guide wire and, using the guide wire, pulling the dilation device through the endoscope and into the non-vascular lumen; removing the needle from the non-vascular lumen while retaining the guide wire in the needle tract; pulling the dilation device up into and partially through the needle tract; inflating a balloon of the dilation device by gradually introducing controlled amounts of a fluid to increase pressure in the balloon so the balloon smoothly and gradually expands the needle tract into a stoma tract while bringing a wall of said non-vascular lumen against an abdominal wall;
   placing a peel-away sheath over the dilation device, deflating the balloon by only a small amount to allow the peel-away sheath to pass over the distal end of the dilation device and through the stoma tract into the non-vascular lumen;
   threading a PEG device over the guide wire and inserting the PEG device through the peel away sheath;
   fully deflating the balloon and withdrawing the balloon through the peel-away sheath; separating the peel-away sheath and removing it.

2. The method of claim 1, wherein the dilation device comprises:
   a tubular support having a length, width, and a longitudinal axis, the tubular support defining a continuous pathway through the device;
   an inflatable dilation balloon oriented axially on the tubular support, the inflatable dilation balloon including an inflatable dilation region forming a first portion of the device and an inflatable retention region forming a second portion of the device; and a balloon inflation lumen,
   wherein the inflatable dilation region has a deflated diameter and an inflated diameter, wherein the inflatable retention region is configured to have a diameter upon full, unrestrained inflation that is greater than the inflated diameter of the inflatable dilation region, and wherein the inflatable retention region is inflated as the inflatable dilation region is inflated.

3. A method of placing a PEG device, the method comprising:
   inserting a needle into a non-vascular lumen of a patient, wherein inserting the needle forms a needle tract;
   introducing a guide wire through the needle;
   securing a dilation device to the end of the guide wire, the dilation device comprising an inflatable dilation balloon including an inflatable dilation region and an inflatable retention region, the dilation region having a deflated diameter and an inflated diameter, the retention region having an inflated diameter that is greater than the inflated diameter of the dilation region;
   using the guide wire, pulling the dilation device into the non-vascular lumen;
   removing the needle from the lumen while retaining the guide wire in the needle tract;
   pulling the dilation device up into and partially through the needle tract;
   inflating the dilation balloon of the dilation device by gradually introducing controlled amounts of a fluid to increase pressure in the dilation balloon so the dilation region of the dilation balloon smoothly and gradually expands the needle tract into a stoma tract while the retention region of the dilation balloon brings a portion of the non-vascular lumen against an abdominal wall and stabilizes the portion of the non-vascular lumen against the abdominal wall;
   fitting a non-vascular catheter tube of a PEG device over the inflated dilation region of the dilation balloon through the dilated stoma tract and into the portion of the non-vascular lumen stabilized by the inflated retention region of the dilation balloon; and
   withdrawing the dilation device to leave the non-vascular catheter tube in the stoma tract.

4. The method of claim 3, further comprising, before fitting the non-vascular catheter tube over the inflated dilation region, deflating the dilation region of the dilation balloon by only a small amount to allow the non-vascular catheter tube to pass over the dilation region of the dilation balloon.

5. The method of claim 3, wherein the retention region and the dilation region of the dilation balloon inflate simultaneously as controlled amounts of the fluid are gradually introduced in the dilation balloon.

6. The method of claim 3, wherein the dilation region of the dilation balloon has a length, and wherein the dilation region has a constant diameter along the length.

7. The method of claim 6, wherein the dilation region inflates radially over the length to provide atraumatic dilation of the needle tract to form the stoma tract.

8. The method of claim 3, wherein the dilation balloon is a single inflatable balloon comprising the dilation region and the retention region.

9. A method of placing a PEG device, the method comprising:
   inserting a needle into a non-vascular lumen of a patient, wherein inserting the needle forms a needle tract;
   positioning an inflatable dilation region of an inflatable dilation device in the needle tract and positioning an inflatable retention region of the dilation device in a non-vascular lumen of the patient;
   inflating the dilation device, wherein inflating the dilation device inflates the dilation region to dilate the needle tract and thereby forms a stoma tract, wherein inflating the retention region brings a portion of the non-vascular lumen against an abdominal wall and stabilizes the portion of the non-vascular lumen against the abdominal wall; and
   inserting a non-vascular catheter tube of the PEG device over the inflated dilation region to place the PEG device in the stoma tract.

10. The method of claim 9, wherein positioning the dilation region of the dilation device in the needle tract comprises pulling the dilation device into and partially through the needle tract such that the dilation region reaches abdominal tissue and skin on an exterior of the patient.

11. The method of claim 9, wherein the dilation region of the dilation device has a length, and wherein the dilation region has a constant diameter along the length.

12. The method of claim 11, wherein the dilation region inflates radially over the length to provide atraumatic dilation of the needle tract to form the stoma tract.

13. The method of claim 9, wherein the dilation device is a single inflatable balloon comprising the dilation region and the retention region.

14. The method of claim 9, further comprising, before positioning the dilation region and the retention region of the dilation device:
  introducing a guide wire through the needle;
  securing the dilation device to the end of the guide wire; and
  using the guide wire, pulling the dilation device into the non-vascular lumen and the needle tract.

15. The method of claim 9, further comprising withdrawing the dilation device to leave the non-vascular catheter tube in the stoma tract.

16. The method of claim 9, wherein the dilation region has a deflated diameter and an inflated diameter, and where the retention region has an inflated diameter that is greater than the inflated diameter of the dilation region.

17. The method of claim 9, wherein inflating the dilation device comprises gradually introducing controlled amounts of a fluid to increase pressure in the dilation device such that the dilation region of the dilation device smoothly and gradually expands the needle tract into a stoma tract while the retention region of the dilation device brings the portion of the non-vascular lumen against the abdominal wall to stabilize the portion of the non-vascular lumen.

18. The method of claim 9, further comprising, before inserting the non-vascular catheter tube over the inflated dilation region, deflating the dilation region of the dilation device by only a small amount to allow the non-vascular catheter tube to pass over the dilation region of the dilation device.

19. The method of claim 9, wherein the retention region and the dilation region of the dilation device inflate simultaneously as controlled amounts of the fluid are graduallly introduced in the dilation device.

* * * * *